United States Patent
Lu

(10) Patent No.: US 12,391,996 B2
(45) Date of Patent: Aug. 19, 2025

(54) EARLY WARNING GENETIC TESTING OF TOXIC CYANOBACTERIA IN WATER SUPPLY

(71) Applicant: USA, represented by Administrator of the U.S. EPA, Washington, DC (US)

(72) Inventor: Jingrang Lu, Mason, OH (US)

(73) Assignee: THE U.S. EPA, Washington, DC (US)

( * ) Notice: Subject to any disclaimer, the term of this patent is extended or adjusted under 35 U.S.C. 154(b) by 165 days.

(21) Appl. No.: 16/142,319

(22) Filed: Sep. 26, 2018

(65) Prior Publication Data
US 2024/0191311 A1  Jun. 13, 2024

(51) Int. Cl.
C12Q 1/689 (2018.01)
A61K 35/748 (2015.01)
C12Q 1/686 (2018.01)

(52) U.S. Cl.
CPC ............ *C12Q 1/689* (2013.01); *A61K 35/748* (2013.01); *C12Q 1/686* (2013.01); *C02F 2307/14* (2013.01); *C12Q 2600/142* (2013.01)

(58) Field of Classification Search
None
See application file for complete search history.

(56) References Cited

FOREIGN PATENT DOCUMENTS

| | | | |
|---|---|---|---|
| CN | 105368950 | A | 3/2016 |
| JP | 2014532438 | A5 | 12/2014 |
| KR | 101484259 | B1 | 1/2015 |
| KR | 101509071 | B1 | 4/2015 |
| WO | 2004104211 | A3 | 3/2005 |
| WO | 2009129558 | A1 | 10/2009 |

OTHER PUBLICATIONS

Al-Tebrineh, Jamal, et al. "A multiplex qPCR targeting hepato-and neurotoxigenic cyanobacteria of global significance." Harmful Algae 15 (2012): 19-25. (Year: 2012).*
Sittampalam et al. Preface. May 1, 2012 [Updated Mar. 31, 2017]. In: Markossian S, Grossman A, Arkin M, et al., editors. Assay Guidance Manual [Internet]. Bethesda (MD): Eli Lilly & Company and the National Center for Advancing Translational Sciences; 2004-. (Year: 2012).*
Kralik et al. A Basic Guide to Real Time PCR in Microbial Diagnostics: Definitions, Parameters, and Everything. Front Microbiol. Feb. 2, 2017;8:108. doi: 10.3389/fmicb.2017.00108. PMID: 28210243; PMCID: PMC5288344. (Year: 2017).*
Yi-Ting Chiu, et al. A qPCR-Based Tool to Diagnose the Presence of Harmful Cyanobacteria and Cyanotoxins in Drinking Water Sources. https://www.ncbi.nlm.nih.gov/pmc/articles/PMC5451997/.

Daniel Tillett, et al. Detection of Toxigenicity by a Probe for the Microcystin Synthetase A Gene (mcyA) of the Cyanobacterial Genus Microcystis: Comparison of Toxicities with 16S rRNA and Phycocyanin Operon (Phycocyanin Intergenic Spacer) Phylogenies. Genetics and Molecular Biology. Mar. 21, 2001. DOI: 10.1128/AEM.67.6.2810-2818.2001 https://aem.asm.org/content/67/6/2810.short.
Michael Hisbergues, et al. PCR-based identification of microcystin-producing genotypes of different cyanobacterial genera. Arch Microbiol (2003) 180: 402. https://doi.org/10.1007/s00203-003-0605-9 https://link.springer.com/article/10.1007/s00203-003-0605-9.
Nonneman and Zimba. A PCR-Based Test to Assess the Potential for Microcystin Occurrence in Channel Catfish Production Ponds. Journal of Phycology. Feb. 19, 2002 https://doi.org/10.1046/.1529-8817.2002.01138.x.
Melanie Kaebernick et al. Light and the Transcriptional Response of the Microcystin Biosynthesis Gene Cluster. Genetics and Molecular Biology. May 2000. DOI: 10.1128/AEM.66.8.3387-3392.2000.
Ngwa, F.F., Madramootoo, C.A. & Jabaji, S. Development and application of a multiplex qPCR technique to detect multiple microcystin-producing cyanobacterial genera in a Canadian freshwater lake. J Appl Phycol (2014) 26: 1675. https://doi.org/10.1007/s10811-013-0199-9.
Ngwa, F., C. Madramootoo & S. Jabaji, 2012. Monitoring toxigenic microcystis strains in the Missisquoi Bay, Quebec, by PCR targeting multiple toxic gene loci. Environmental Toxicology. doi: 10.1002/tox.21770.
Jamal Al-Tebrineh, et al. Community Composition, Toxigenicity, and Environmental Conditions during a Cyanobacterial Bloom Occurring along 1,100 Kilometers of the Murray River. Appl. Environ. Microbiol. Dec. 2011, 78 (1) 263-272; DOI: 10.1128/AEM.05587-11.
Anne Rantala-Ylinen, et al. Anatoxin—a synthetase gene cluster of the cyanobacterium Anabaena strain 37 and molecular methods to detect potential producers. Applied and Environmental Microbiology Aug. 2011, AEM.06022-11; DOI: 10.1128/AEM.06022-11.
Yongguang Jiang, et al. Sporadic distribution and distinctive variations of cylindrospermopsin genes in cyanobacterial strains and environmental samples from Chinese freshwater bodies. Appl. Environ. Microbiol. Jun. 2014, AEM.00551-14; DOI: 10.1128/AEM.00551-14.

\* cited by examiner

*Primary Examiner* — Aaron A Priest
*Assistant Examiner* — Tian Yu
(74) *Attorney, Agent, or Firm* — Stein IP, LLC

(57) ABSTRACT

This invention is at least one panel of qPCR/RT-qPCR assays which enables simultaneous testing for the presence of multiple species and subgroups of cyanobacteria that produce microcystin, anatoxin, saxitoxin, and cylindrospermopsin cyanotoxins. The method takes into account that some cyanobacteria species may carry genes associated with multiple toxin types. Testing for each toxin type is conducted under standardized test conditions which allow quantification of the number of gene copies present for cyanotoxins which may contribute to the overall toxin level.

17 Claims, 8 Drawing Sheets
Specification includes a Sequence Listing.

| Cyanotoxin | Associated Cyanobacteria Genera | Common Consensus Sequence (5' to 3') |
|---|---|---|
| Microcystin | Microcystis, Nostoc, Planktothrix, Synecococcus, Anabaena, Aphanizomenon | AAAAGTGTTTATTAGCGGCTCATTTCGGGTATTAAGTTTACT GAATAATCAGAGGGGATATTGTTACAGGTTTAGTCTCTAATGGA CGGTTAGA |
| Cylindrospermopsin | Anabaena, Aphanizomenon, Cylindrospermopsis, Raphidiopsis | AACACGGCTTTGAGGTCTATCCAATTCCCTTTCGCAATGTCTT TGAGTTTGGCGGTTCGCTCCATTGTGCCACCTGGGATATCCA TCGCACGGGAACCTGTGAGGATTACTTC |
| Anatoxin | Anabaena, Aphanizomenon | TGCTGGCTATTACAACCTCTATGGTCCGACGGAGACAAATGT CTGCACATATTACCGAGTCTCACCGCCCGATATTGAAACAAGT GAAGCAGTTCCTATTGGACAAGCC |
| Saxitoxin | Anabaena, Aphanizomenon | GCGGGACTTTATGCTCTACTACTGTACCCTGAAAGGCGGCAT TGAGAGGCGTGGGTGTAACTCGCTGTCGCAATTATGTCAA TTATTCCCAAATGCCGATGACGGAGTA |

FIG 2

| Targeted Gene | mcyA (microcystin) | anaC (anatoxin) | sxtA (saxitoxin) | cyrA (cylindrospermopsin) |
|---|---|---|---|---|
| Targeted Genus/Genera | ALL | Anabaena, Aphanizomenon | Anabaena, Aphanizomenon | Anabaena, Aphanizomenon, Cylindrospermopsis, Raphidiopsis |
| Forward Primer (5' to 3') | AAAAGTGTTTTATTAGCGGGCTCATT (SEQ ID NO:1) | TGCTGGCTATTACAACCTCTATG (SEQ ID NO:21) | GCGGGGACTTTATGCTCTACTAC (SEQ ID NO:23) | AACACGGCTTTGAGGTCTATC (SEQ ID NO:10) |
| Reverse Primer (5' to 3') | TCTAACCGTCCATTAGAGACTAAACC (SEQ ID NO:2) | CAGGCTTGTCCAATAGGAACT (SEQ ID NO:22) | TACTCCGTCATCGGCATTTG (SEQ ID NO:24) | GAAGTAATCCTCACAGGTTCCC (SEQ ID NO:28) |
| Optional Probe (from 5' to 3') | FAM/TACCGAGTCTCACCGCCCGATATT/IABKFQ (SEQ ID NO:38) | | FAM/ATTGAGAGCGTGGTGGGTGTAACT/IABKFQ (SEQ ID NO:39) | |

FIG. 3

| Targeted Gene | Targeted Genus/Genera | Forward Primer (5' to 3') | Reverse Primer (5' to 3') | Optional Probe (from 5' to 3') |
|---|---|---|---|---|
| mcyE | Anabaena | GCT CCA GGT GTG ATT GAA TTT ATA G | GCA TAG CGG CTA ATT TGG TAT TC | FAM/AG GTC AAT GG CTA TCG TGT AGA TCC AGG /IABkFQ |
| mcyE | Anabaena | CTG CAC ACA ACA CCA TCT ATT TAC | GAT CGC AGT TTC TCG GTC TAA T | FAM/T AACACTGCTGTCACCGAG TTGCC/IABkFQ |
| mcyA | Nostoc | CCC ATC TAC CAC GAT GTC TTT AC | CAC TGC ATG GCT ATT GAC TAC T | FAM/TA AAG CCT GG AGG TTG AGA GTG GC/IABkFQ |
| mcyE | Nostoc | TGCGAACTGCTGCCATAAGGAAT | CAGCAAATGCAACAC GGAAT | FAM/TAATATTGCGGCAGAAACG GCTGC/IABkFQ |
| mcyA | Microcystis | CTGAATAATCAGAGGGAT ATTGTTACG | CTCCAGATAACTCTAA ACGTAGGG | AATGGACGGTTAGAAGCAGCCG AT |
| mcyE | Microcystis | CTG CTC AAC CCT TAA GTC TAG G | CGA CTA ATA CGG CGG CTA AA | FAM/TG AGT TAT GG AGT TGA AGA AAG CCT CGA /IABkFQ |
| mcyA | Planktothrix | TTA CAG CTA ACG GGT GGA AC | GTA ACT CCG CTA AGG GAT AAC G | FAM/TT GCA ACG GA ACG GGA TAG TCT GG/IABkFQ |
| mcyA | Synecococcus | ATG GCC CTA TTC AAA GGT CAG | CCA TCT GCG CAA ACA ACA G | FAM/CA CTG CGT T/ZEN/C CAT TTC TGC GAT GC/IABkFQ |
| mcyE | Synecococcus, Planktothrix | CAC TCA ATG AAA CCG GGA AAT C | CCG ATG GGA TGT TTG GTT AGA | FAM/CC CAA GTA AA TTA TGT TGC ACC GCG T/IABkFQ |
| geoA | Anabaena | CAA AGA GAG GTG GAA GAG GAA G | GGGTCTACTCCATACT CCTCAA | FAM/TT GAA TGT GA GTA CCC AAG AGG CCG /IABkFQ |
| geoA | Aphanizomenon | GCTAACCTCACTAACGAA CTACTC | GAG AAC ATT CAC ACG CTC TACT | FAM/GA ACA CTG CT GTC ACT GAA TTA CCC TCT /IABkFQ |
| anaC | Anabaena, Aphanizomenon | TGC TGG CTA TTA CAA CCT CTA TG | CAG GCT TGT CCA ATA GGA ACT | FAM/TA CCG AGT CT CAC CGC CCG ATA TT/IABkFQ |
| sxtA | Aphanizomenon | CGC TAT ACC CAC GGA TTT GTT | GGG ATC AGC AGT AGT CCA TCT A | |
| cyrA | Anabaena, Aphanizomenon, Cylindrospermopsis, Raphidiopsis | AACACGGCTTTGAGGTCT ATC | GAAGTAATCCTCACAG GTTCCC | |
| pstS | Anabaena, Aphanizomenon | TGG AAT GTT ACC AGC AGG AAT AA | AGT GCT GCT TGA CGT AAA CT | |
| nif | Anabaena | ATG CCT ATC CGT GAA GGT AAA G | CCA CCG GAG TGA GCA TAT TT | |
| nif | Nostoc | ATC GTT CAA CAC GCA GAA TTG | TCA TCC ATT TCG ATA GGT GTG G | |

FIG 4

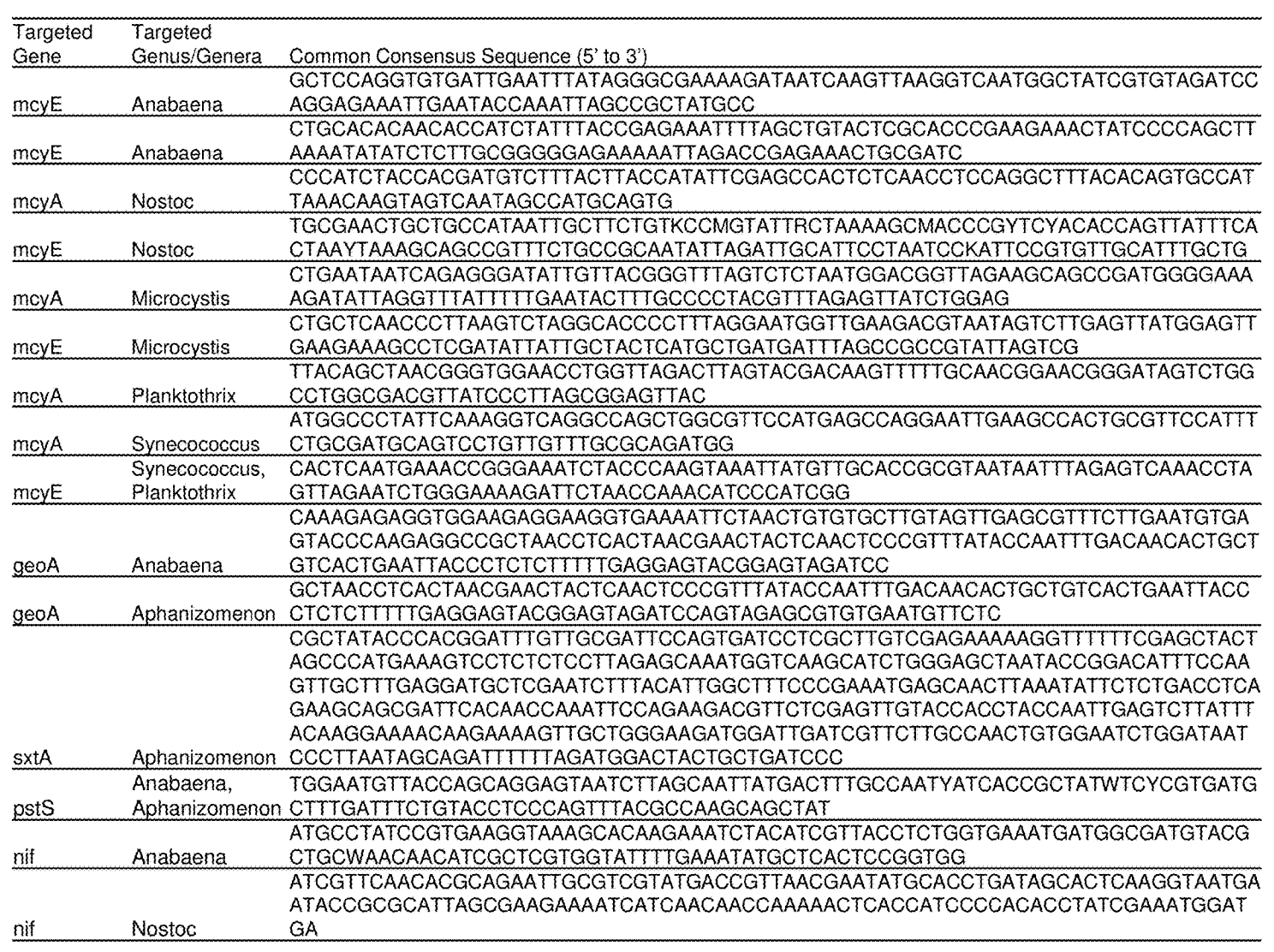

| Targeted Gene | Targeted Genus/Genera | Common Consensus Sequence (5' to 3') |
|---|---|---|
| mcyE | Anabaena | GCTCCAGGTGTGATTGAATTTATAGGGCGAAAAGATAATCAAGTTAAGGTCAATGGCTATCGTGTAGATCC AGGAGAAATTGAATACCAAATTAGCCGCTATGCC |
| mcyE | Anabaena | CTGCACACAACACCATCTATTACCGAGAAATTAGCTGTACTCGCACCGAAGAAACTATCCCCAGCTT AAATATATCTCCACCAGATGTCTTACTTACCATATTCGAGCCACTCCAAGCTTTACACAGTGCCAT |
| mcyA | Nostoc | CCCATCTACCACGATGTCTTACTTACCATATTCGAGCCACTCCAAGCTTTACACAGTGCCAT TAAACAAGTAGTCAATAGCCATGCAGT

# EARLY WARNING GENETIC TESTING OF TOXIC CYANOBACTERIA IN WATER SUPPLY

STATEMENT REGARDING FEDERALLY SPONSORED RESEARCH OR DEVELOPMENT

The invention described herein was made by an employee of the United States Government and may be manufactured and used by the Government of the United States of America for governmental purposes without the payment of any royalties. This and related patents are available for licensing to qualified licensees. Please contact Carmen Krieger at 202.564.0396 for more information.

INCORPORATION OF SEQUENCE LISTING

Incorporated by reference in its entirety herein is a computer-readable nucleotide sequence listing submitted concurrently herewith and identified as follows: One 12,418 Byte ASCII (Text) file named "EPA_800-17_SEQ.txt," created on Aug. 29, 2018.

FIELD OF INVENTION

The present invention relates to nucleic acid products used in the analysis of nucleic acids, such as primers or probes for detection or identification of organisms for bacteria, and more specifically to an assay for simultaneously conducting testing for a plurality of cyanobacteria which carry a gene to produce a toxin, using standardized test conditions.

BACKGROUND OF THE INVENTION

The U.S. Environmental Protection Agency (EPA) publishes an annual list of the top thirty unregulated contaminants that are known or expected to occur in public water systems in the U.S. Ten of the thirty contaminants of concern are toxins produced by a common type of bacteria called cyanobacteria.

Cyanobacteria, also called blue-green algae, are microscopic organisms found naturally in all types of water. A "cyanobacterial bloom" is an event during which cyanobacteria, multiply very quickly. Blooms can form in warm, slow-moving waters that are rich in nutrients from fertilizer runoff or septic tank overflows, and most often occur in late summer or early fall.

A harmful cyanobacterial bloom is an event associated with elevated cyanotoxin levels that are either deemed unsafe or require further monitoring. Exposure to high cyanotoxin levels causes damage to liver cells and neural signaling pathways in humans, as well as less severe effects such as skin rashes. These events occur on a global basis at great risk to local populations. For example, in 2014, a toxic bloom left 500,000 people in Ohio without drinking water. In 2014, a toxic bloom caused Florida to declare a state of emergency.

Most cyanobacterial blooms do not produce toxins at a sufficient level to compromise public water supplies and cause harm to humans and other species. Additionally, the vast majority of cyanobacteria species do not carry the gene necessary to produce toxins. However, several types of cyanobacteria carry genes which produce one or more types of toxins during a bloom. The aggregate level of all types of cyanotoxins produced by all species known to be carriers may cause the toxin level to exceed a safe threshold for humans and other species.

Historically, water supplies have been monitored by measuring cyanobacteria count and biomass to determine the presence of cyanobacterial species and their blooms, without differentiating species that carry harmful toxin genes or the types of toxins produced.

More recently, assays have been developed to test for genes associated with microcystin, anatoxin, saxitoxin and cylindrospermopsin by performing quantitative polymerase chain reaction (qPCR) and reverse transcription qPCR (RT-qPCR) methods known in the art. These test methods known in the art can detect the presence of a single toxin gene type produced by multiple species.

RT-qPCR and qPCR testing must be performed under different time and temperature conditions for each toxin type, and testing methods must be further differentiated for individual species. The number of gene copies detected can be correlated to future levels for the individual toxin. However, the test conditions of each assay used to test an individual toxin gene are not uniform, and the quantifications produced using each assay are not statistically comparable. Therefore, the results cannot be aggregated to predict a total toxin level.

There is an unmet need for a single assay kit which can simultaneously test for multiple common types of cyanotoxin producing genes across diverse species. There is a further unmet need for testing methods that can be used to accurately determine the probability that a cyanobacteria bloom will result in cyanotoxin levels that exceed US EPA 10-day health advisory levels for drinking water.

SUMMARY OF THE INVENTION

This invention is a system comprised of quantitative polymerase chain reaction (qPCR) and reverse transcription qPCR (RT-qPCR) assays for detecting the presence of cyanotoxin genes. In various embodiments, the invention includes one or two panels of assays for screening and early warning and for toxic group identification.

The invention enables simultaneous testing for the presence of cyanobacteria genes associated with four toxins which contribute to the cyanotoxin level in a water supply, and the presence of dominant toxic cyanobacterial groups which may trigger the need for an EPA Health Advisory alert. The toxin types associated with the tested genes are anatoxin, microcystin, saxitoxin and cylindrospermopsin. The invention includes qPCR assay panels comprised of separate assays to simultaneously detect each toxin type and toxic group. The assays operate under standardized test conditions. The standardized test conditions include a uniform annealing temperature, thermocycle duration and control samples having common parameters. Results obtained using these standardized conditions can be used to determine the aggregate number of gene copies present in a sample for the four toxin types tested.

In various embodiments, the assay contained in each assay panel has a common annealing temperature of approximately 62 degrees Celsius.

In various embodiments, the method of use includes steps for producing mathematically comparable test results for each toxin quantifying the number of cyanotoxin gene copies detected by each assay and producing test data which may be aggregated for multiple toxin types.

TERMS OF ART

As used herein, the term, "aggregate number of gene copies" means the total number of gene copies present in a sample for the four toxins tested which contribute to overall toxin levels.

As used herein, the term, "comparable test results" means test data which is obtained under standardized test conditions so that it is mathematically comparable and may be aggregated and analyzed relative to multiple toxin types.

As used herein, the term, "standardized test conditions" means a set of common parameters for multiple qPCR/RT-qPCR tests which results in comparable test results.

BRIEF DESCRIPTION OF THE DRAWINGS

FIG. 2 is a table identifying multiple cyanotoxin types, the carrier group of cyanobacteria associated with each cyanotoxin gene, and the common DNA sequences which define a member of the cyanobacteria carrier group.

FIG. 3 is a table illustrating exemplary primer and probe sequences which can be used to produce a CTP Assay Panel for early detection and warning.

FIG. 4 is a table illustrating primer and probe sequences which can be used to produce a CTP Assay Panel for detecting dominant toxic groups of cyanobacteria.

FIG. 5 illustrates the common genetic sequences which are detected by the primers and probes used to produce a CTP Assay Panel for detecting dominant toxic groups of cyanobacteria.

DETAILED DESCRIPTION OF THE INVENTION

Figure 1:
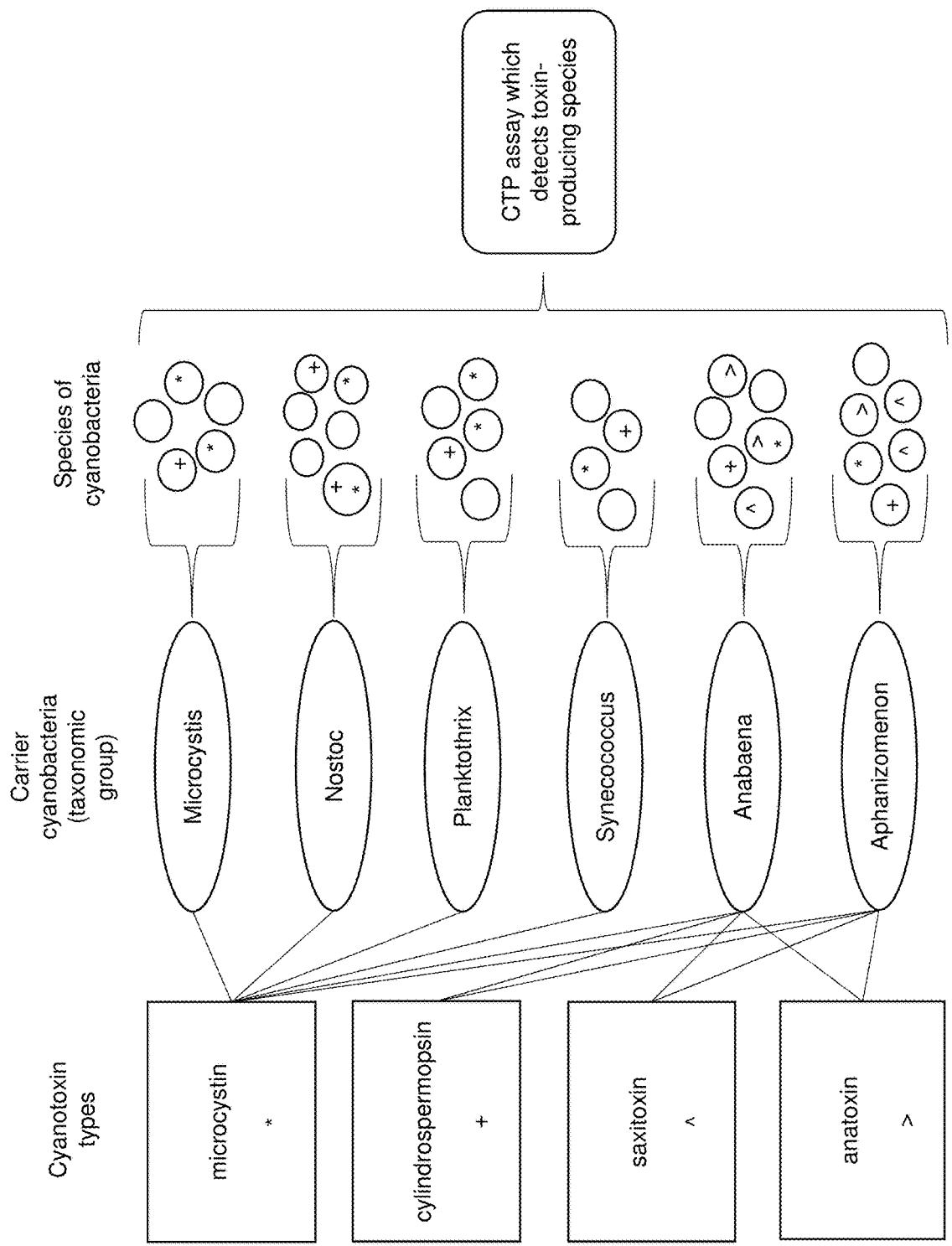
FIG. 1 is a diagram which illustrates how a Cyanotoxin Prediction (CTP) Assay Panel can be used to more accurately detect the presence of toxin-producing cyanobacteria in a water sample.

FIG. 1 is a diagram which illustrates how one exemplary embodiment of a Cyanotoxin Prediction (CTP) Assay Panel can be used to more accurately detect the presence of toxin-producing cyanobacteria in a water sample.

FIG. 1 illustrates four known types of cyanotoxins (microcystin, anatoxin, saxitoxin, and cylindrospermopsin) which are produced by more than one subgroup of cyanobacteria, represented as ovals. Each subgroup of cyanobacteria includes multiple species, represented as circles; however, only a few of these species produce cyanotoxins. Species carrying toxic genes that produce cyanotoxins are represented by an asterisk or symbol in the circle.

In the exemplary embodiment shown, the CTP Assay Panel distinguishes between toxic and non-toxic species to specifically detect the presence of toxic species.

The CTP Assay Panel identifies and distinguishes the presence of toxic subgroups of cyanobacteria through the use of novel oligonucleotide primers and quantitative polymerase chain reaction (qPCR) amplification methods known in the art.

FIG. 2 is a table identifying multiple cyanotoxins, the carrier group of cyanobacteria associated with each cyanotoxin gene, and the common DNA sequences which define a member of the cyanobacteria carrier group.

The right-most column illustrates the common DNA sequences identified by the invention. These sequences, also called consensus sequences, are common in multiple species and allow simultaneous testing for four different toxin genes to simultaneously detect the presence of multiple species that produce cyanotoxins.

FIG. 3 is a table illustrating exemplary primer and probe sequences which can be used to produce CTP Assay Panel 100 for early detection and warning.

In one exemplary embodiment, CTP Assay Panel 100 is a panel of RT-qPCR/qPCR assays for detecting cyanotoxin genes, which include the novel primer pairs described in FIG. 3. In this embodiment, the primer pairs are designed to detect multiple species of toxic cyanobacteria simultaneously. The primers shown each have a sequence that will bind to a cyanotoxin gene at 60-64 degrees Celsius. In various embodiments, the recommended annealing temperature for the primers shown is 62 degrees Celsius. This common annealing temperature allows all assays to be conducted simultaneously. Without these novel primers and standardized conditions for multiple species, it was not possible to integrate all of the test results for multiple species. Standardized qPCR reaction conditions produce statistically comparable qPCR data from samples with different species, taken from geographically diverse waters.

In this exemplary embodiment, the assays are standardized with the same common annealing temperature, thermocycle duration, and control samples designed to yield consistent qPCR test results. In various embodiments, CTP Assay Panel 100 further includes approximately four to six positive control samples, each having a unique number of cyanotoxin gene copies within a range of approximately 1,000 to 10,000 DNA gene copies per liter.

In one embodiment, simultaneous detection of the mcyE/mcyA, sxtA, cyrA, or anaC genes indicates possible production of microcystin, saxitoxin, cylindrospermopsin or anatoxin, respectively. In this exemplary embodiment, the RT-qPCR/qPCR assay detects the presence of cyanotoxin genes in control samples and collected water samples or other test samples. In various embodiments, CTP Assay 100 can be used to determine the total number of gene copies for each cyanotoxin gene and estimate the population size of each group of toxic cyanobacteria.

In the exemplary embodiment shown, each primer pair selected for qPCR analysis targets a sequence of cyanotoxin biosynthesis genes and genus-specific genes that is common to multiple cyanobacteria species. The target genes encode cyanotoxins, including microcystin, anatoxin, saxitoxin, and cylindrospermopsin. Targeted genes include an mcyA gene sequence carried by cyanobacteria in all six genera, an anaC gene sequence carried by cyanobacteria in the *Anabaena* and *Aphanizomenon* genera (exemplary detected species include *Aphanizomenon gracile, Anabaena* sp., and *Anabaena circinalis*), an sxtA gene sequence carried by cyanobacteria in the *Anabaena* and *Aphanizomenon* genera, and a cyrA gene sequence carried by cyanobacteria in the *Anabaena, Aphanizomenon, Cylindrospermopsis,* and *Raphidiopsis* genera (exemplary detected species include *Raphidiopsis curvata* and *Cylindrospermopsis raciborskii*).

FIG. 4 is a table illustrating primer and probe sequences which can be used to produce CTP Assay Panel 200 for identifying dominant toxic groups of cyanobacteria.

CTP Assay Panel 200 can detect multiple toxic species simultaneously. In various embodiments, CTP Assay Panel 200 can detect the number of toxic gene copies and predict the level of toxin that will be produced by each type of cyanobacteria individually and in the aggregate.

In an alternative embodiment, CTP Assay Panel 200 is comprised of a panel of multiple RT-qPCR/qPCR assays that include the primers shown in FIG. 4A. In this embodiment, the RT-qPCR/qPCR assay detects the presence or absence of individual toxin-producing subtypes of cyanobacteria to determine dominant toxic groups in control samples and collected water samples or other test samples. This embodiment more specifically determines which individual subtypes of cyanobacteria are present and which has the highest population. Each primer shown has an annealing temperature of approximately 60 to 64 degrees Celsius. In various embodiments, the recommended annealing temperature for the primers shown is 62 degrees Celsius.

In the alternative embodiment, alternative primer pairs can detect an mcyA or mcyE gene sequence carried by cyanobacteria in the *Anabaena, Nostoc, Microcystis, Planktothrix*, and *Synecococcus* genera (exemplary detected species include *Anabaena* sp., *Anabaenopsis elenkinii, Anabaena lemmermannii, Anabaena flos-aquae, Nostoc* sp., *Fischerella* sp., *Nodularia spumigena, Nodularia sphaerocarpa, Nodularia* sp., *Microcystis* sp., *M. aeruginosa, M. viridis, M. panniformis, M. wesenbergii, M. smithii, Planktothrix* sp., *P. rubescens, P. agardhii, Synechococcus* sp., WH 8103, and WH8102), an anaC gene sequence carried by cyanobacteria in the *Anabaena*, and *Aphanizomenon* genera, an sxtA gene sequence carried by cyanobacteria in the *Aphanizomenon* genus, a cyrA gene sequence carried by cyanobacteria in the *Anabaena, Aphanizomenon, Cylindrospermopsis*, and *Raphidiopsis* genera (exemplary detected species include *Raphidiopsis curvata* and *Cylindrospermopsis raciborskii*), a geoA gene sequence carried by cyanobacteria in the *Anabaena* and *Aphanizomenon* genera (exemplary detected species include *Dolichospermum ucrainicum, D. planctonicum, D. circinale, Nicotiana attenuate*, and *Anabaena ucrainica*), a pstS phosphase gene sequence carried by cyanobacteria in the *Anabaena* and *Aphanizomenon* genera, and a nif gene sequence carried by cyanobacteria in the *Anabaena* and *Nostoc* genera.

FIG. 5 illustrates the common genetic sequences which are detected by the primers and probes used to produce CTP Assay Panel 200 for identifying dominant toxic groups of cyanobacteria.

FIG. 5 illustrates the common DNA sequences which define a member of the cyanobacteria carrier group detected by the CTP Assay Panel 200 primers and probes.

The exemplary common microcystin sequences shown in FIG. 2 and FIG. 5 are listed as <SEQ ID NO. 52> through <SEQ ID NO. 61> in the sequence listing file. Exemplary common anatoxin sequences are listed as <SEQ ID NO. 64>. Exemplary common saxitoxin sequences are listed as <SEQ ID NO. 65> and <SEQ ID NO. 66>. Exemplary common cylindrospermopsin sequences are listed as <SEQ ID NO. 67>. Exemplary common geoA sequences are listed as <SEQ ID NO. 62> and <SEQ ID NO. 63>.

Figure 6:
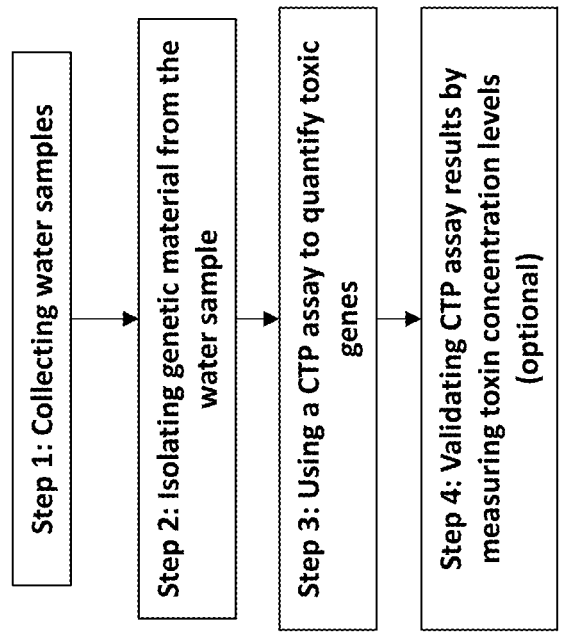
FIG. 6 illustrates an exemplary method of using a CTP Assay Panel and correlating CTP Assay Panel results to subsequently measured cyanotoxin levels.

FIG. 6 illustrates exemplary Method 300 for using CTP Assay Panel 100 and/or 200 to measure cyanotoxin genes and correlating CTP Assay results to subsequently measured cyanotoxin levels.

In the exemplary embodiment shown, Method 300 utilizes a panel of novel qPCR/RT-qPCR assays for simultaneously detecting microcystin, anatoxin, saxitoxin, and cylindrospermopsin genes in cyanobacteria. The invention is a testing method for detecting specific bacterial groups associated with toxin production.

In various embodiments, Method 300 may be used to identify the number of gene copies present and predict the amount of toxin that will be produced by each cyanobacteria genus individually and in the aggregate. In various embodiments, Method 300 utilizes analysis of the qPCR/RT-qPCR results to predict whether cyanotoxin concentrations in a source of water will be exceed a toxic threshold deemed harmful to humans and other species within a specified period of time. In various embodiments, the toxic threshold is a limit set by U.S. EPA Drinking Water Health Advisories. For example, the threshold for combined microcystin toxins is 0.3 μg/liter and a gene copy number of 1,000 to 10,000 DNA gene copies per liter predicts that the toxic threshold will be exceeded seven days after measuring the gene copy number.

Step 1 is the step of collecting water samples. In various embodiments, this step is accomplished by periodically collecting water samples from the same source, at various points in time.

Step 2 is the step of isolating genetic material from a water sample.

In one exemplary embodiment this step is accomplished by dividing samples 100-300 mL aliquots and individually filtering the aliquots using EMD Millipore DuraporeTM membrane filters (0.40 μm, MilliPore, Foster City, CA) for DNA extraction. In one embodiment, DNA and RNA are extracted using a kit known in the art, such as AllPrep DNA (QIAGEN, Valencia, CA). Filtered aliquots are stored at −80° C. in 1.5 mL microtubes with lysis buffer prior to extracting DNA and RNA.

In various embodiments, this step includes using any method known in the art for isolating or extracting genetic material from a water sample and conducting reverse transcription to create template DNA from RNA.

Step 3 is the step of using CTP Assay Panel 100 and/or 200 to determine the number of copies of toxic genes.

To conduct a qPCR/RT-qPCR assay, components are combined and heated to create a polymerase chain reaction. In one exemplary embodiment, each reaction contains 1 μM concentration of each selected primer, 2 μl of template DNA from either the sample or the control, a 0.2 mM concentration of each of the four deoxynucleoside triphosphates (dTTP, dCTP, dGTP, and dATP), 1.5 mM MgCl2, 1 μM (each) primer, and 2.5 U of TaqDNA polymerase (Clone Tech, Mountain View, CA) in a total volume of 25 μl. In various embodiments, the effective primer concentration range for the PCR reaction is approximately 0.5 to 1 μM. In this embodiment, the reactions are heated and cooled during 25 cycles of temperature changes, wherein each cycle includes 1 minute of denaturation at 94° C., 1 minute of primer annealing at 62° C., and 5 minutes of primer extension at 72° C. In various embodiments, the annealing temperature is approximately 60 to 64° C.

In various embodiments, this step further includes analyzing the results by methods known in the art to determine the gene copy number ($X_{gene}$) in each sample, for each cyanotoxin gene detected in that sample. In various embodiments, this step may include running CTP Assay Panel 100 and/or 200 on a Juno robot platform where 40 assays can be run at one time, including 1,600 reactions.

Step 4 is the optional step of validating CTP Assay Panel 100 and/or 200 results by measuring toxin concentration levels on a subsequent date using a testing method known in the art and comparing the measured toxin concentration levels to the results of CTP Assay Panel 100.

Figure 7:
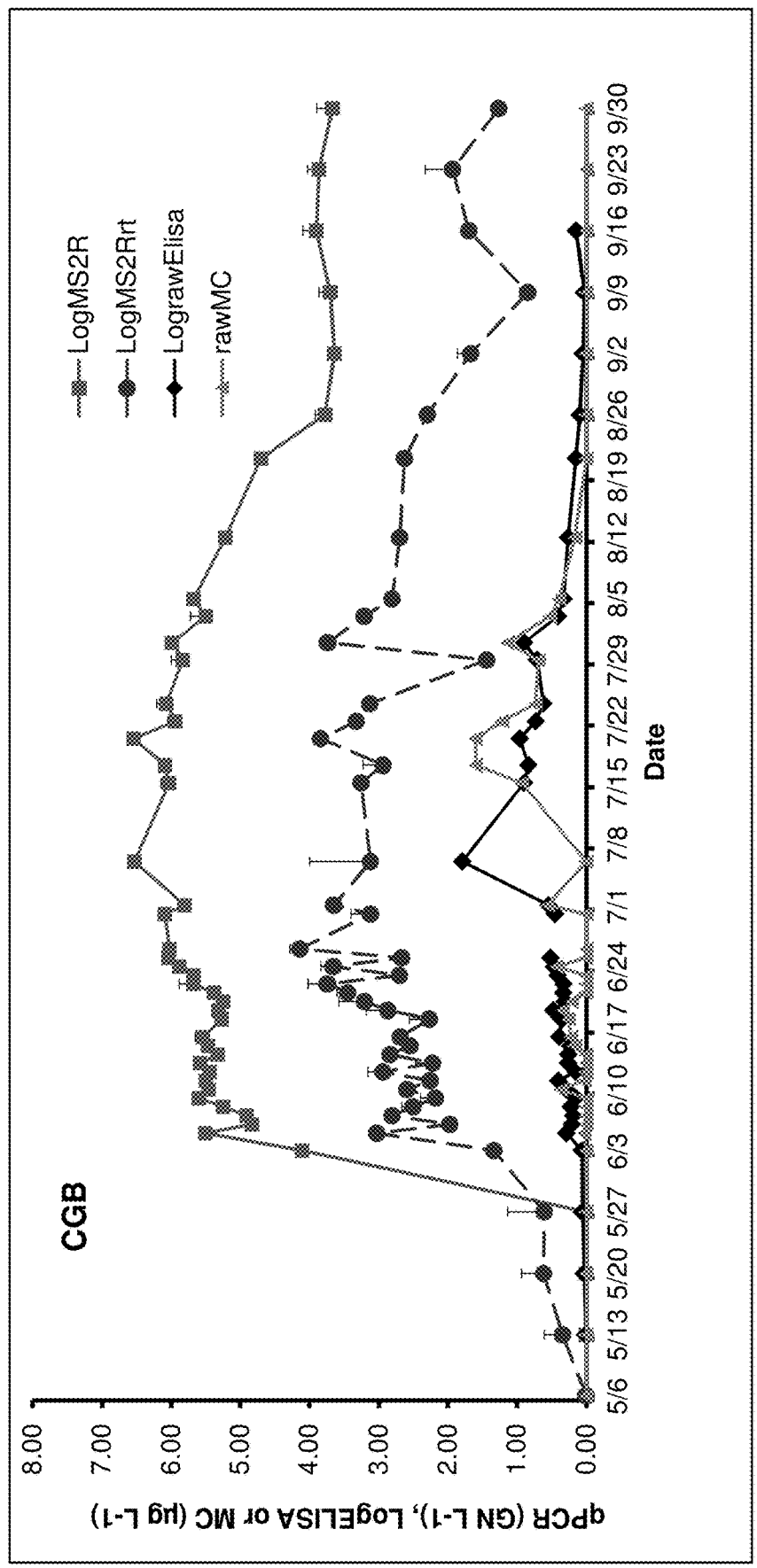
FIG. 7 summarizes exemplary data reporting the number of toxic gene copies and the concentration of cyanotoxins measured during periodic testing of a water source.

FIG. 7 summarizes exemplary data reporting the number of toxic gene copies and the concentration of cyanotoxins measured during periodic testing of a water source. FIG. 7 summarizes the number of toxic gene copies in DNA isolated from a water source and measured once per week between May 6 and September 30. Data marked LogMS2R were measured by a quantitative polymerase chain reaction (qPCR) assay (represented by squares) and data marked LogMS2Rrt were measured by a reverse transcription quantitative polymerase chain reaction (RT-qPCR) assay (represented by circles).

In the exemplary embodiment shown, the concentration of cyanotoxins in a water source was measured by an enzyme-linked immunosorbent assay (ELISA), represented by diamonds. The raw concentration of cyanotoxins measured by ELISA is represented by triangles.

The x-axis shows dates and the y-axis shows gene copy number or toxin concentration on a logarithmic scale.

In alternative embodiments, the concentration of cyanotoxins in a water source is measured by liquid chromatography-tandem mass spectrometry (LC-MS/MS).

Figure 8:
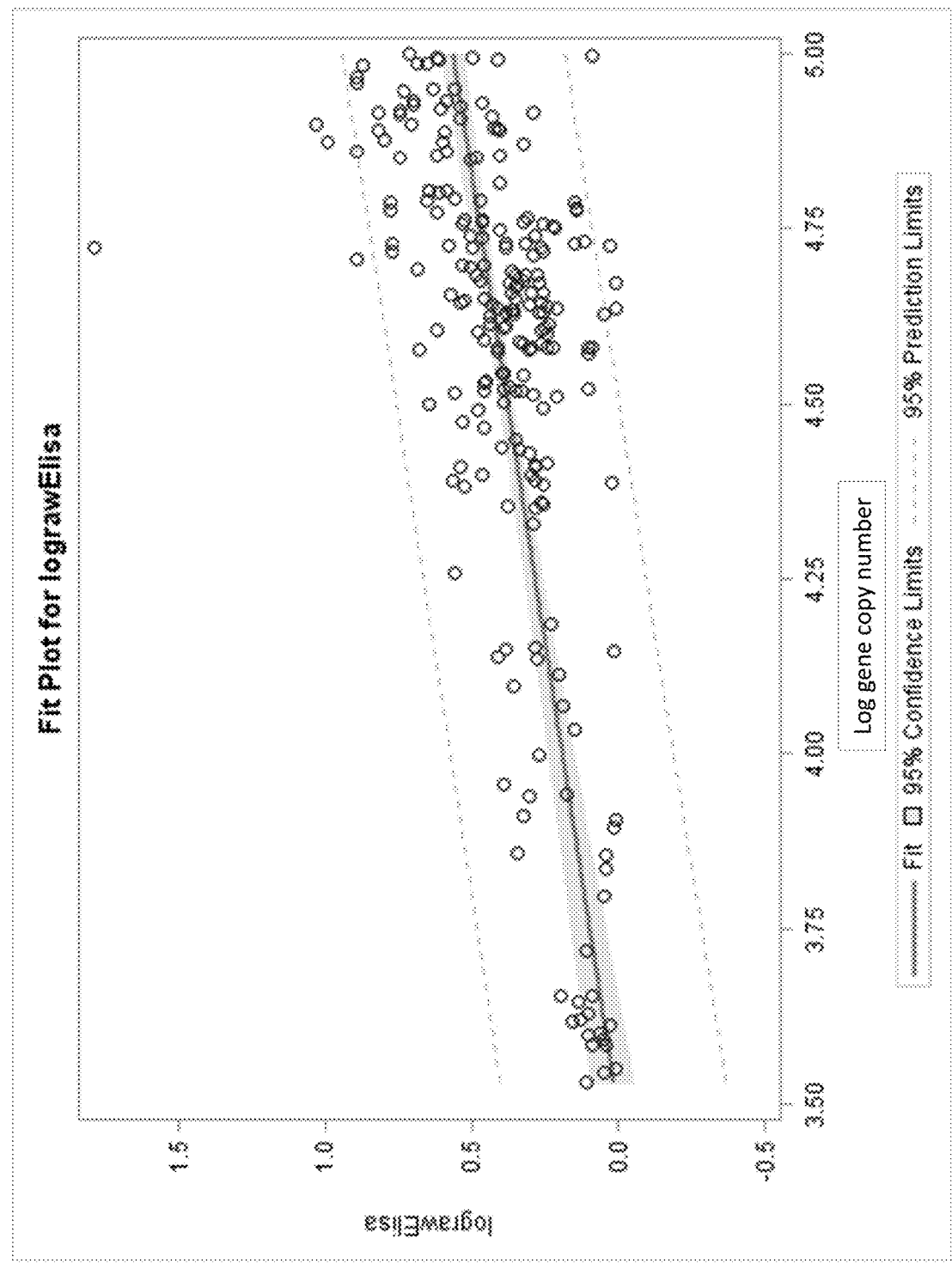
FIG. 8 summarizes exemplary data correlating the number of toxic gene copies measured by the CTP Assay Panel to the subsequent concentration of cyanotoxins measured by an enzyme-linked immunosorbent assay (ELISA).

FIG. 8 summarizes exemplary data correlating the number of toxic gene copies measured by CTP Assay Panel 100 and/or 200 to the subsequent concentration of cyanotoxins measured by an enzyme-linked immunosorbent assay (ELISA).

FIG. 8 shows a regression, which is the best fit curve, of the correlation between the number of toxic gene copies measured by qPCR and RT-qPCR and the concentration of cyanotoxins in a water source measured by an enzyme-linked immunosorbent assay (ELISA). FIG. 8 demonstrates that there is a direct correlation between the expression of the toxic gene and the production of the toxin. The gene copy number is plotted on the x-axis on a logarithmic scale and the associated cyanotoxin concentration measured seven days after the gene copy number from the same water source is plotted on the y-axis on a logarithmic scale. In the exemplary embodiment shown, measured data are represented by open circles. The best fit curve showing a predicted toxin concentration on the y-axis for a given gene copy number measured by CTP Assay Panel 100 or 200 is represented by a dark, thin solid line. The 95% confidence interval of the best fit curve is represented by a thicker, lighter line. The 95% prediction limits showing a range of toxin concentration levels predicted by a given gene copy number are represented as dashed lines.

What is claimed is:

1. A qPCR and/or RT-qPCR cyanotoxin detection apparatus, comprising:
   a first set of primers, comprising a first primer consisting of the sequence set forth in SEQ ID NO:1 and a second primer consisting of the sequence set forth in SEQ ID NO:2;
   a second set of primers, comprising a third primer consisting of the sequence set forth in SEQ ID NO:21 and fourth primer consisting of the sequence set forth in SEQ ID NO:22;
   a third set of primers, comprising a fifth primer consisting of the sequence set forth in SEQ ID NO: 23 and a sixth primer consisting of the sequence set forth in SEQ ID NO:24;
   a fourth set of primers, comprising a seventh primer consisting of the sequence set forth in SEQ ID NO:27 and an eighth primer consisting of the sequence set forth in SEQID NO: 28, and
   at least one probe comprising a detectable label.

2. The apparatus of claim 1, wherein said sets of primers are each present in the apparatus at a concentration of 1 µM.

3. The apparatus of claim 1, wherein said primers hybridize under conditions in which oligonucleotide hybridization occurs with cyanobacterial genes produced by bacteria selected from the group consisting of: Microcystis, Nostoc, Planktothrix, Synecococcus, Anabaena, Aphanizomenon, Raphidiopsis, Cylindrospermopsis, Anabaena sp., Anabaenopsis elenkinii, Anabaena lemmermannii, Anabaena flos-aquae, Nostoc sp., Fischerella sp., Nodularia spumigena, Nodularia sphaerocarpa, Nodularia sp., Microcystis sp., M. aeruginosa, M. viridis, M. panniformis, M. wesenbergii, M. smithil, Planktothrix sp., P. rubescens, P. agardhii, Synechococcus sp., Raphidiopsis curvata, Cylindrospermopsis raciborskil, Dolichospermum ucrainicum, D. planctonicum, D. circinale, Nicotiana attenuate, Anabaena ucrainica, Aphanizomenon gracile, and Anabaena circinalis.

4. A method of detecting the presence of toxic cyanobacterial genes in fresh water supplies, which comprises:
   providing a qPCR and/or RT-qPCR cyanotoxin detection apparatus, wherein said cyanotoxin detection apparatus comprises:
   a first set of primers, comprising a first primer consisting of the sequence set forth in SEQ ID NO:1 and a second primer consisting of the sequence set forth in SEQ ID NO:2;
   a second set of primers, comprising a third primer consisting of the sequence set forth in SEQ ID NO:21 and fourth primer consisting of the sequence set forth in SEQ ID NO:22;

a third set of primers, comprising a fifth primer consisting of the sequence set forth in SEQ ID NO:23 and a sixth primer consisting of the sequence set forth in SEQ ID NO:24:
a fourth set of primers, comprising a seventh primer consisting of the sequence set forth in SEQ ID NO:27 and an eighth primer consisting of the sequence set forth in SEQ ID NO:28, and
at least one probe comprising a detectable label; and
performing the steps of simultaneously:
performing a first qPCR assay with the first set of primers for detecting a microcystin gene;
performing a second qPCR assay with the second set of primers for detecting an anatoxin gene;
performing a third qPCR assay with the third set of primers for detecting a saxitoxin gene; and
performing a fourth qPCR assay with the fourth set of primers for detecting a cylindrospermopsin gene.

5. The method of claim 4, which further comprises the step of selecting at least one primer pair for detecting a microcystin gene from the group of primer pairs consisting of:
forward primer consisting of the sequence set forth in SEQ ID NO:1 and reverse primer consisting of the sequence set forth in SEQ ID NO:2;
forward primer consisting of the sequence set forth in SEQ ID NO:3 and reverse primer consisting of the sequence set forth in SEQ ID NO:4;
forward primer
consisting of the sequence set forth in SEQ ID NO:5 and reverse primer consisting of the sequence set forth in SEQ ID NO:6;
forward primer consisting of the sequence set forth in SEQ ID NO:7 and reverse primer consisting of the sequence set forth in SEQ ID NO:8;
forward primer consisting of the sequence set forth in SEQ ID NO:9 and reverse primer consisting of the sequence set forth in SEQ ID NO10;
forward primer
consisting of the sequence set forth in SEQ ID NO:11 and reverse primer consisting of the sequence set forth in SEQ ID NO:12;
forward primer
consisting of the sequence set forth in SEQ ID NO:13 and reverse primer consisting of the sequence set forth in SEQ ID NO:14;
forward primer consisting of the sequence set forth in SEQ ID NO:15 and reverse
primer consisting of the sequence set forth in SEQ ID NO:16;
forward primer
consisting of the sequence set forth in SEQ ID NO:17 and reverse primer consisting of the sequence set forth in SEQ ID NO:18; and
forward primer
consisting of the sequence set forth in SEQ ID NO:19 and reverse primer consisting of the sequence set forth in SEQ ID NO:20.

6. The method of claim 4, which each primer is present at concentration of 1 µM.

7. The method of claim 4, which further comprises obtaining one or more values reflecting a copy number, $X_{gene}$, of at least one cyanotoxin gene present in at least one of said fresh water supplies, wherein said cyanotoxin gene is selected from a group consisting of microcystin, anatoxin, saxitoxin, and cylindrospermopsin.

8. The apparatus of claim 1, wherein the apparatus further comprises a membrane filter and a DNA extraction kit, wherein the membrane filter possesses a pore size of 0.40 µm.

9. The apparatus of claim 2, wherein the apparatus further comprises:
(i) dTTP, dCTP, dGTP, and dATP,
(ii) $MgCl_2$, and
(iii) TaqDNA polymerase.

10. The apparatus of claim 8, wherein the apparatus further comprises:
(i) dTTP, dCTP, dGTP, and dATP,
(ii) $MgCl_2$, and
(iii) TaqDNA polymerase.

11. A kit for detecting the presence of cyanobacterial toxins in a sample by qPCR and/or RT-qPCR assay, comprising:
a first set of primers, comprising a first primer consisting of the sequence set forth in SEQ ID NO: 1 and a second primer consisting of the sequence set forth in SEQ ID NO:2;
a second set of primers, comprising a third primer consisting of the sequence set forth in SEQ ID NO:21 and fourth primer consisting of the sequence set forth in SEQ ID NO:22;
a third set of primers, comprising a fifth primer consisting of the sequence set forth in SEQ ID NO: 23 and a sixth primer consisting of the sequence set forth in SEQ ID NO:24;
a fourth set of primers, comprising a seventh primer consisting of the sequence set forth in SEQ ID NO:27 and an eighth primer consisting of the sequence set forth in SEQIDNO: 28;
a mixture of dTTP, dCTP, dGTP, and dATP,
a solution of $MgCl_2$,
TaqDNA polymerase, and
at least one probe comprising a detectable label,
wherein the cyanobacterial toxins are microcystin, anatoxin, saxitoxin, and cylindrospermopsin.

12. The kit of claim 10, wherein the primers in each of the sets of primer are present in an amount of 1 µM each.

13. The kit of claim 11, further comprising a membrane filter and a DNA extraction kit, wherein the membrane filter possesses a pore size of 0.40 µm.

14. The kit of claim 11, further comprising one or more positive control samples corresponding to each of the cyanobacterial toxins.

15. The kit of claim 11, further comprising four to six positive control samples corresponding to each of the cyanobacterial toxins.

16. The kit of claim 11, wherein the kit detects the presence of the cyanobacterial toxins in a single reaction under a single set of reaction conditions comprising an annealing temperature and thermocycle duration.

17. The kit of claim 15, wherein the presence of cyanobacterial toxins is detected by quantitation of an aggregate number of gene copies corresponding to the cyanobacterial toxins present in the sample.

* * * * *

SEQUENCE LISTING

```
<160> NUMBER OF SEQ ID NOS: 67

<210> SEQ ID NO 1
<211> LENGTH: 25
<212> TYPE: DNA
<213> ORGANISM: Cyanobacteria

<400> SEQUENCE: 1
aaaagtgttt tattagcggc tcatt                                    25

<210> SEQ ID NO 2
<211> LENGTH: 26
<212> TYPE: DNA
<213> ORGANISM: Cyanobacteria

<400> SEQUENCE: 2
tctaaccgtc cattagagac taaacc                                   26

<210> SEQ ID NO 3
<211> LENGTH: 24
<212> TYPE: DNA
<213> ORGANISM: Cyanobacteria

<400> SEQUENCE: 3
ctgcacacaa caccatctat ttac                                     24

<210> SEQ ID NO 4
<211> LENGTH: 22
<212> TYPE: DNA
<213> ORGANISM: Cyanobacteria

<400> SEQUENCE: 4
gatcgcagtt tctcggtcta at                                       22

<210> SEQ ID NO 5
<211> LENGTH: 25
<212> TYPE: DNA
```

```
<213> ORGANISM: Cyanobacteria

<400> SEQUENCE: 5
gctccaggtg tgattgaatt tatag                                           25

<210> SEQ ID NO 6
<211> LENGTH: 23
<212> TYPE: DNA
<213> ORGANISM: Cyanobacteria

<400> SEQUENCE: 6
gcatagcggc taatttggta ttc                                             23

<210> SEQ ID NO 7
<211> LENGTH: 23
<212> TYPE: DNA
<213> ORGANISM: Cyanobacteria

<400> SEQUENCE: 7
cccatctacc acgatgtctt tac                                             23

<210> SEQ ID NO 8
<211> LENGTH: 22
<212> TYPE: DNA
<213> ORGANISM: Cyanobacteria

<400> SEQUENCE: 8
cactgcatgg ctattgacta ct                                              22

<210> SEQ ID NO 9
<211> LENGTH: 18
<212> TYPE: DNA
<213> ORGANISM: Cyanobacteria

<400> SEQUENCE: 9
tgcgaactgc tgccataa                                                   18

<210> SEQ ID NO 10
<211> LENGTH: 20
<212> TYPE: DNA
<213> ORGANISM: Cyanobacteria

<400> SEQUENCE: 10
cagcaaatgc aacacggaat                                                 20

<210> SEQ ID NO 11
<211> LENGTH: 27
<212> TYPE: DNA
<213> ORGANISM: Cyanobacteria

<400> SEQUENCE: 11
ctgaataatc agagggatat tgttacg                                         27

<210> SEQ ID NO 12
<211> LENGTH: 24
<212> TYPE: DNA
<213> ORGANISM: Cyanobacteria

<400> SEQUENCE: 12
ctccagataa ctctaaacgt aggg                                            24

<210> SEQ ID NO 13
<211> LENGTH: 22
```

```
<212> TYPE: DNA
<213> ORGANISM: Cyanobacteria

<400> SEQUENCE: 13
ctgctcaacc cttaagtcta gg                                            22

<210> SEQ ID NO 14
<211> LENGTH: 20
<212> TYPE: DNA
<213> ORGANISM: Cyanobacteria

<400> SEQUENCE: 14
cgactaatac ggcggctaaa                                               20

<210> SEQ ID NO 15
<211> LENGTH: 20
<212> TYPE: DNA
<213> ORGANISM: Cyanobacteria

<400> SEQUENCE: 15
ttacagctaa cgggtggaac                                               20

<210> SEQ ID NO 16
<211> LENGTH: 22
<212> TYPE: DNA
<213> ORGANISM: Cyanobacteria

<400> SEQUENCE: 16
gtaactccgc taagggataa cg                                            22

<210> SEQ ID NO 17
<211> LENGTH: 21
<212> TYPE: DNA
<213> ORGANISM: Cyanobacteria

<400> SEQUENCE: 17
atggccctat tcaaaggtca g                                             21

<210> SEQ ID NO 18
<211> LENGTH: 19
<212> TYPE: DNA
<213> ORGANISM: Cyanobacteria

<400> SEQUENCE: 18
ccatctgcgc aaacaacag                                                19

<210> SEQ ID NO 19
<211> LENGTH: 22
<212> TYPE: DNA
<213> ORGANISM: Cyanobacteria

<400> SEQUENCE: 19
cactcaatga aaccgggaaa tc                                            22

<210> SEQ ID NO 20
<211> LENGTH: 21
<212> TYPE: DNA
<213> ORGANISM: Cyanobacteria

<400> SEQUENCE: 20
ccgatgggat gtttggttag a                                             21

<210> SEQ ID NO 21
```

```
<211> LENGTH: 23
<212> TYPE: DNA
<213> ORGANISM: Cyanobacteria

<400> SEQUENCE: 21
tgctggctat tacaacctct atg                                          23

<210> SEQ ID NO 22
<211> LENGTH: 21
<212> TYPE: DNA
<213> ORGANISM: Cyanobacteria

<400> SEQUENCE: 22
caggcttgtc caataggaac t                                            21

<210> SEQ ID NO 23
<211> LENGTH: 22
<212> TYPE: DNA
<213> ORGANISM: Cyanobacteria

<400> SEQUENCE: 23
gcgggacttt atgctctact ac                                           22

<210> SEQ ID NO 24
<211> LENGTH: 20
<212> TYPE: DNA
<213> ORGANISM: Cyanobacteria

<400> SEQUENCE: 24
tactccgtca tcggcatttg                                              20

<210> SEQ ID NO 25
<211> LENGTH: 21
<212> TYPE: DNA
<213> ORGANISM: Cyanobacteria

<400> SEQUENCE: 25
cgctataccc acggatttgt t                                            21

<210> SEQ ID NO 26
<211> LENGTH: 22
<212> TYPE: DNA
<213> ORGANISM: Cyanobacteria

<400> SEQUENCE: 26
gggatcagca gtagtccatc ta                                           22

<210> SEQ ID NO 27
<211> LENGTH: 21
<212> TYPE: DNA
<213> ORGANISM: Cyanobacteria

<400> SEQUENCE: 27
aacacggctt tgaggtctat c                                            21

<210> SEQ ID NO 28
<211> LENGTH: 22
<212> TYPE: DNA
<213> ORGANISM: Cyanobacteria

<400> SEQUENCE: 28
gaagtaatcc tcacaggttc cc                                           22
```

```
<210> SEQ ID NO 29
<211> LENGTH: 28
<212> TYPE: DNA
<213> ORGANISM: Cyanobacteria

<400> SEQUENCE: 29
aggtcaatgg ctatcgtgta gatccagg                                28

<210> SEQ ID NO 30
<211> LENGTH: 24
<212> TYPE: DNA
<213> ORGANISM: Cyanobacteria

<400> SEQUENCE: 30
taacactgct gtcaccgagt tgcc                                    24

<210> SEQ ID NO 31
<211> LENGTH: 24
<212> TYPE: DNA
<213> ORGANISM: Cyanobacteria

<400> SEQUENCE: 31
taaagcctgg aggttgagag tggc                                    24

<210> SEQ ID NO 32
<211> LENGTH: 24
<212> TYPE: DNA
<213> ORGANISM: Cyanobacteria

<400> SEQUENCE: 32
taatattgcg gcagaaacgg ctgc                                    24

<210> SEQ ID NO 33
<211> LENGTH: 24
<212> TYPE: DNA
<213> ORGANISM: Cyanobacteria

<400> SEQUENCE: 33
aatggacggt tagaagcagc cgat                                    24

<210> SEQ ID NO 34
<211> LENGTH: 28
<212> TYPE: DNA
<213> ORGANISM: Cyanobacteria

<400> SEQUENCE: 34
tgagttatgg agttgaagaa agcctcga                                28

<210> SEQ ID NO 35
<211> LENGTH: 24
<212> TYPE: DNA
<213> ORGANISM: Cyanobacteria

<400> SEQUENCE: 35
ttgcaacgga acgggatagt ctgg                                    24

<210> SEQ ID NO 36
<211> LENGTH: 24
<212> TYPE: DNA
<213> ORGANISM: Cyanobacteria

<400> SEQUENCE: 36
cactgcgttc catttctgcg atgc                                    24
```

```
<210> SEQ ID NO 37
<211> LENGTH: 26
<212> TYPE: DNA
<213> ORGANISM: Cyanobacteria

<400> SEQUENCE: 37
cccaagtaaa ttatgttgca ccgcgt                                        26

<210> SEQ ID NO 38
<211> LENGTH: 24
<212> TYPE: DNA
<213> ORGANISM: Cyanobacteria

<400> SEQUENCE: 38
taccgagtct caccgcccga tatt                                          24

<210> SEQ ID NO 39
<211> LENGTH: 24
<212> TYPE: DNA
<213> ORGANISM: Cyanobacteria

<400> SEQUENCE: 39
attgagagcg tggtgggtgt aact                                          24

<210> SEQ ID NO 40
<211> LENGTH: 22
<212> TYPE: DNA
<213> ORGANISM: Cyanobacteria

<400> SEQUENCE: 40
caaagagagg tggaagagga ag                                            22

<210> SEQ ID NO 41
<211> LENGTH: 22
<212> TYPE: DNA
<213> ORGANISM: Cyanobacteria

<400> SEQUENCE: 41
gggtctactc catactcctc aa                                            22

<210> SEQ ID NO 42
<211> LENGTH: 25
<212> TYPE: DNA
<213> ORGANISM: Cyanobacteria

<400> SEQUENCE: 42
ttgaatgtga gtacccaaga ggccg                                         25

<210> SEQ ID NO 43
<211> LENGTH: 24
<212> TYPE: DNA
<213> ORGANISM: Cyanobacteria

<400> SEQUENCE: 43
gctaacctca ctaacgaact actc                                          24

<210> SEQ ID NO 44
<211> LENGTH: 22
<212> TYPE: DNA
<213> ORGANISM: Cyanobacteria

<400> SEQUENCE: 44
gagaacattc acacgctcta ct                                            22
```

<210> SEQ ID NO 45
<211> LENGTH: 28
<212> TYPE: DNA
<213> ORGANISM: Cyanobacteria

<400> SEQUENCE: 45
caacactgct gtcactgaat taccctct                                28

<210> SEQ ID NO 46
<211> LENGTH: 23
<212> TYPE: DNA
<213> ORGANISM: Cyanobacteria

<400> SEQUENCE: 46
tggaatgtta ccagcaggaa taa                                     23

<210> SEQ ID NO 47
<211> LENGTH: 20
<212> TYPE: DNA
<213> ORGANISM: Cyanobacteria

<400> SEQUENCE: 47
agtgctgctt gacgtaaact                                         20

<210> SEQ ID NO 48
<211> LENGTH: 22
<212> TYPE: DNA
<213> ORGANISM: Cyanobacteria

<400> SEQUENCE: 48
atgcctatcc gtgaaggtaa ag                                      22

<210> SEQ ID NO 49
<211> LENGTH: 20
<212> TYPE: DNA
<213> ORGANISM: Cyanobacteria

<400> SEQUENCE: 49
ccaccggagt gagcatattt                                         20

<210> SEQ ID NO 50
<211> LENGTH: 21
<212> TYPE: DNA
<213> ORGANISM: Cyanobacteria

<400> SEQUENCE: 50
atcgttcaac acgcagaatt g                                       21

<210> SEQ ID NO 51
<211> LENGTH: 22
<212> TYPE: DNA
<213> ORGANISM: Cyanobacteria

<400> SEQUENCE: 51
tcatccattt cgataggtgt gg                                      22

<210> SEQ ID NO 52
<211> LENGTH: 95
<212> TYPE: DNA
<213> ORGANISM: Cyanobacteria

<400> SEQUENCE: 52

```
aaaagtgttt tattagcggc tcattttcgg gtattaagtt tactgaataa tcagagggat    60
attgttacag gtttagtctc taatggacgg ttaga                               95

<210> SEQ ID NO 53
<211> LENGTH: 105
<212> TYPE: DNA
<213> ORGANISM: Cyanobacteria

<400> SEQUENCE: 53
gctccaggtg tgattgaatt tatagggcga aaagataatc aagttaaggt caatggctat    60
cgtgtagatc caggagaaat tgaataccaa attagccgct atgcc                   105

<210> SEQ ID NO 54
<211> LENGTH: 120
<212> TYPE: DNA
<213> ORGANISM: Cyanobacteria

<400> SEQUENCE: 54
ctgcacacaa caccatctat ttaccgagaa attttagctg tactcgcacc cgaagaaact    60
atccccagct taaatatat ctcttgcggg ggagaaaaat tagaccgaga aactgcgatc    120

<210> SEQ ID NO 55
<211> LENGTH: 99
<212> TYPE: DNA
<213> ORGANISM: Cyanobacteria

<400> SEQUENCE: 55
cccatctacc acgatgtctt tacttaccat attcgagcca ctctcaacct ccaggcttta    60
cacagtgcca ttaaacaagt agtcaatagc catgcagtg                           99

<210> SEQ ID NO 56
<211> LENGTH: 142
<212> TYPE: DNA
<213> ORGANISM: Cyanobacteria

<400> SEQUENCE: 56
tgcgaactgc tgccataatt gcttctgtkc cmgtattrct aaaagcmacc cgytcyacac    60
cagttatttc actaaytaaa gcagccgttt ctgccgcaat attagattgc attcctaatc   120
ckattccgtg ttgcatttgc tg                                            142

<210> SEQ ID NO 57
<211> LENGTH: 124
<212> TYPE: DNA
<213> ORGANISM: Cyanobacteria

<400> SEQUENCE: 57
ctgaataatc agagggatat tgttacgggt ttagtctcta atggacggtt agaagcagcc    60
gatggggaaa agatattagg tttatttttg aatactttgc ccctacgttt agagttatct   120
ggag                                                                124

<210> SEQ ID NO 58
<211> LENGTH: 129
<212> TYPE: DNA
<213> ORGANISM: Cyanobacteria

<400> SEQUENCE: 58
ctgctcaacc cttaagtcta ggcaccccctt taggaatggt tgaagacgta atagtcttga    60
gttatggagt tgaagaaagc ctcgatatta ttgctactca tgctgatgat ttagccgccg   120
```

```
tattagtcg                                                               129

<210> SEQ ID NO 59
<211> LENGTH: 100
<212> TYPE: DNA
<213> ORGANISM: Cyanobacteria

<400> SEQUENCE: 59
ttacagctaa cgggtggaac ctggttagac ttagtacgac aagttttgc aacggaacgg        60 gatagtctgg cctggcgacg ttatcccta gcggagttac                              100

<210> SEQ ID NO 60
<211> LENGTH: 102
<212> TYPE: DNA
<213> ORGANISM: Cyanobacteria

<400> SEQUENCE: 60
atggccctat tcaaaggtca ggccagctgg cgttccatga gccaggaatt gaagccactg       60
cgttccattt ctgcgatgca gtcctgttgt ttgcgcagat gg                          102

<210> SEQ ID NO 61
<211> LENGTH: 112
<212> TYPE: DNA
<213> ORGANISM: Cyanobacteria

<400> SEQUENCE: 61
cactcaatga aaccgggaaa tctacccaag taaattatgt tgcaccgcgt aataatttag       60
agtcaaacct agttagaatc tgggaaaaga ttctaaccaa acatcccatc gg               112

<210> SEQ ID NO 62
<211> LENGTH: 185
<212> TYPE: DNA
<213> ORGANISM: Cyanobacteria

<400> SEQUENCE: 62
caaagagagg tggaagagga aggtgaaaat tctaactgtg tgcttgtagt tgagcgtttc       60
ttgaatgtga gtacccaaga ggccgctaac ctcactaacg aactactcaa ctcccgttta       120
taccaatttg acaacactgc tgtcactgaa ttaccctctc tttttgagga gtacggagta      180
gatcc                                                                   185

<210> SEQ ID NO 63
<211> LENGTH: 123
<212> TYPE: DNA
<213> ORGANISM: Cyanobacteria

<400> SEQUENCE: 63
gctaacctca ctaacgaact actcaactcc cgtttatacc aatttgacaa cactgctgtc       60
actgaattac cctctctttt tgaggagtac ggagtagatc cagtagagcg tgtgaatgtt      120
ctc                                                                     123

<210> SEQ ID NO 64
<211> LENGTH: 109
<212> TYPE: DNA
<213> ORGANISM: Cyanobacteria

<400> SEQUENCE: 64
tgctggctat tacaacctct atggtccgac ggagacaaat gtctgcacat attaccgagt       60
```

```
ctcaccgccc gatattgaaa caagtgaagc agttcctatt ggacaagcc        109

<210> SEQ ID NO 65
<211> LENGTH: 111
<212> TYPE: DNA
<213> ORGANISM: Cyanobacteria

<400> SEQUENCE: 65
gcgggacttt atgctctact actgtaccct gaaaggcggc attgagagcg tggtgggtgt     60
aactcgctgt cgcaattatg tcaattattc ccaaatgccg atgacggagt a             111

<210> SEQ ID NO 66
<211> LENGTH: 395
<212> TYPE: DNA
<213> ORGANISM: Cyanobacteria

<400> SEQUENCE: 66
cgctataccc acggatttgt tgcgattcca gtgatcctcg cttgtcgaga aaaaggtttt     60
ttcgagctac tagcccatga aagtcctctc tccttagagc aaatggtcaa gcatctggga   120
gctaataccg gacatttcca agttgctttg aggatgctcg aatctttaca ttggctttcc   180
cgaaatgagc aacttaaata ttctctgacc tcagaagcag cgattcacaa ccaaattcca   240
gaagacgttc tcgagttgta ccacctacca attgagtctt atttacaagg aaaacaagaa   300
aagttgctgg gaagatggat tgatcgttct tgccaactgt ggaatctgga taatcccta    360 atagcagatt ttttagatgg actactgctg atccc                              395

<210> SEQ ID NO 67
<211> LENGTH: 113
<212> TYPE: DNA
<213> ORGANISM: Cyanobacteria

<400> SEQUENCE: 67
aacacggctt tgaggtctat ccaattccct ttcgcaatgt ctttgagttt ggcggttcgc     60
tccattgtgc cacctgggat atccatcgca cgggaacctg tgaggattac ttc           113
```